United States Patent
Hoyer et al.

(10) Patent No.: US 7,754,719 B2
(45) Date of Patent: Jul. 13, 2010

(54) SUBSTITUTED PIPERIDINE DERIVATIVES AS SOMATOSTATIN SST1 RECEPTOR ANTAGONISTS

(75) Inventors: Daniel Hoyer, St. Louis (FR); Konstanze Hurth, Saint Louis (FR); Thomas J. Troxler, Wahlen b. Laufen (CH)

(73) Assignee: Novartis AG, Basel (CH)

( * ) Notice: Subject to any disclaimer, the term of this patent is extended or adjusted under 35 U.S.C. 154(b) by 74 days.

(21) Appl. No.: 11/995,725

(22) PCT Filed: Jul. 13, 2006

(86) PCT No.: PCT/EP2006/006867

§ 371 (c)(1),
(2), (4) Date: Jun. 3, 2008

(87) PCT Pub. No.: WO2007/009662

PCT Pub. Date: Jan. 25, 2007

(65) Prior Publication Data

US 2008/0255142 A1    Oct. 16, 2008

(30) Foreign Application Priority Data

Jul. 15, 2005  (GB) .................. 0514615.4

(51) Int. Cl.
*A61K 31/5025* (2006.01)
*A61K 31/496* (2006.01)
*C07D 407/06* (2006.01)
*C07D 413/06* (2006.01)
*C07D 413/14* (2006.01)
*C07D 487/04* (2006.01)
*C07D 513/04* (2006.01)

(52) U.S. Cl. ............... 514/248; 514/253.04; 514/253.1; 514/253.11; 544/236; 544/362; 544/364

(58) Field of Classification Search ............. None
See application file for complete search history.

(56) References Cited

FOREIGN PATENT DOCUMENTS

| EP | 0445701 A1 | 9/1991 |
| EP | 1086947 A1 | 3/2001 |
| WO | 98/18786 A1 | 5/1998 |
| WO | 03/022214 A2 | 3/2003 |
| WO | 03/040125 A1 | 5/2003 |
| WO | 2004/011430 A1 | 2/2004 |

OTHER PUBLICATIONS

Thermos et al. Pharmacology & Therapeutics vol. 110, p. 455-464 (2006).*

* cited by examiner

*Primary Examiner*—Emily Bernhardt
(74) *Attorney, Agent, or Firm*—John Alexander

(57) ABSTRACT

Compound of the formula (I) wherein $R^1$, $R^2$, n and m are as defined in the specification. The compounds of formula (I) are somatostatin sst1 receptor antagonists.

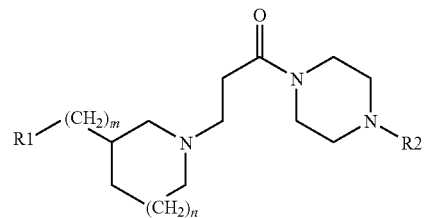

(I)

5 Claims, No Drawings

SUBSTITUTED PIPERIDINE DERIVATIVES AS SOMATOSTATIN SST1 RECEPTOR ANTAGONISTS

This application is the National Stage of Application No. PCT/EP2006/006867, filed on Jul. 13, 2006, which claims benefit of GB 0514615.4 filed Jul. 15, 2005. The contents of both are incorporated herein by reference in their entirety.

SUMMARY OF THE INVENTION

The present invention relates to 3-substituted piperidine derivatives, their preparation, their use as or in pharmaceuticals and pharmaceutical compositions comprising them.

BACKGROUND OF THE INVENTION

A number of compounds having sst1 antagonistic activity are known, e.g. from International Application WO 03/40125.

A problem to be solved by the present invention is to provide further compounds with this activity and/or other useful pharmaceutical activities and properties.

A novel class of compounds has been found that solves this problem and shows pharmaceutical usefulness as described in more detail below.

DETAILED DESCRIPTION OF THE INVENTION

The present invention relates especially to a compound of formula I

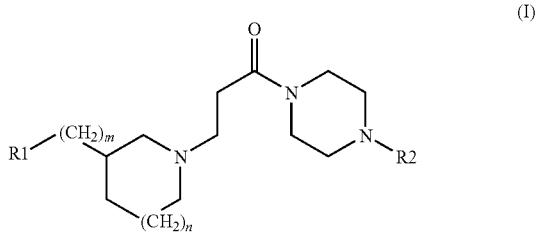

(I)

wherein

R1 is unsubstituted or substituted aryl, unsubstituted or substituted heterocyclyl;

R2 is unsubstituted or substituted aryl or unsubstituted or substituted heterocyclyl;

and each of n and m, independently of the other, is 0, 1 or 2;

or a salt thereof.

In addition, the present invention relates to methods for the manufacture or a compound of the formula I or a salt thereof, the use of a compound of the formula I, or a salt thereof, in the therapeutic and/or diagnostic treatment of the animal or human body or for the manufacture of pharmaceuticals, a method of treatment comprising administering a compound of the formula I, or a salt thereof, to an animal or a human, and pharmaceutical compositions comprising them, as well as to other embodiments of the invention given below in more detail.

Unless otherwise indicated, the general terms and names used in the description of the pre-sent invention preferably have the following meanings (where more specific definitions, in each case separately, or in combination, may be used to replace more general terms in order to define more preferred embodiments of the invention):

The term "lower" or "$C_1$-$C_7$-" defines a moiety with up to and including maximally 7, especially up to and including maximally 4, carbon atoms, said moiety being branched or straight-chained. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl.

In unsubstituted or substituted aryl, aryl is preferably a mono-, bi- or tricyclic aromatic hydro-carbon group with 6 to 14 ring carbon atoms, especially phenyl, naphthyl or fluorenyl, each of which is unsubstituted or substituted by one or more, especially 1 to 3, substituents independently selected preferably from alkyl, preferably $C_1$-$C_7$-alkyl, such as methyl, ethyl, n-propyl, isopropyl, n-butyl, isobutyl, tert-butyl, pentyl or hexyl (especially n-hexyl); cycloalkyl, especially $C_3$-$C_8$-cycloalkyl; phenyl or (1- or 2-) napthyl, each of which is unsubstituted or substituted with one or more, especially up to three, substituents selected from $C_1$-$C_7$-alkyl, halo-$C_1$-$C_7$-alkyl, such as trifluoromethyl, $C_1$-$C_7$-alkoxy, such as methoxy, halo-$C_1$-$C_7$-alkoxy, such as trifluoromethoxy, nitro, cyano, and halo; unsubstituted, $C_1$-$C_7$-alkoxy-substituted or halosubstituted phenyl-$C_1$-$C_7$-alkyl; hydroxy; hydroxy-$C_1$-$C_7$-alkyl; alkoxy, preferably $C_1$-$C_7$-alkoxy, especially methoxy; phenoxy; alkanoyloxy, especially $C_1$-$C_7$-alkanoyloxy; $C_1$-$C_7$-alkanoylthio; halo; amino; N-mono- or N,N-di-($C_1$-$C_7$-alkyl)amino; $C_1$-$C_7$-alkanoylamino; $C_1$-$C_7$-alkanoyl; carboxy; $C_1$-$C_7$-alkoxycarbonyl; cyano; carbamoyl, N-mono- or N,N-di-($C_1$-$C_7$-alkyl)carbamoyl; $C_1$-$C_7$-alkylsulfonyl; sulfamoyl; and nitro. Very preferred as unsubstituted or substituted aryl is phenyl that is unsubstituted or substituted by one or more, especially up to three, substituents as described above for aryl, especially cyano, $C_1$-$C_7$-alkoxy, nitro and/or especially halo. Examples of preferred unsubstituted or substituted aryl moieties are 3-fluoro-4-nitrophenyl, 4-cyanophenyl, 3,4-difluorophenyl, 4-cyano-2,6-difluorophenyl, 4-nitro-phenyl, 4-fluorophenyl or (especially 9-) fluorenyl.

In unsubstituted or substituted heterocyclyl, heterocyclyl is preferably a ring with 3 to 20, preferably 5 to 14 ring atoms which is unsaturated, partially saturated or saturated, has one to four, preferably one to three heteroatoms independently selected from O, N (or NH) and S, is mono-, bi- or tricylic, e.g. a monocyclic heterocycle with 3 to 8, preferably 5 to 7, ring members annealed to one or two rings independently selected from benzo, pyridino, pyrazino, pyrimidino or pyridazino, and is unsubstituted or substituted by one or more, specially up to three moieties independently selected from those mentioned above as substituents for substituted aryl and oxo; unsubstituted or substituted heterocyclyl is, preferably, a moiety selected from (i) pyridinyl, especially 2-pyridinyl; (ii) substituted pyridinyl wherein the substituents are independently selected from one or more, especially one or two of hydroxy, halo, nitro, cyano, trifluoromethyl, $C_1$-$C_4$-alkyl and $C_1$-$C_4$-alkoxy, especially alkoxy-pyridinyl, especially $C_1$-$C_7$-alkoxy-pyridin-2-, -3- or -4-yl, or dialkoxy-pyridinyl, especially di-($C_1$-$C_7$-alkoxy)-pyridin-2-, -3- or -4-yl; (iii) 1-alkyl-oxo-dihydropyridinyl, especially 1-($C_1$-$C_7$-alkyl)-6-oxo-1,6-dihydropyridin-2-yl; (iv) benzo[1,2,5]oxadiazolyl, especially benzo[1,2,5]oxadiazol-5- or -6-yl; (v) benzo[1,2,5]thiadiazolyl, especially benzo[1,2,5]thiadiazol-5- or -6-yl; (vi) imidazo[1,2-b]pyridazin-8-, -7- or preferably -6-yl; (vii) 4-[1,2,5]-thiadiazolo-[3,4-b]pyridin-7-, -6- or -5-yl, (viii) xanthenyl, especially xanthen-9-yl; (ix) thioxanthenyl, especially thioxanthen-9-yl; (x) benzo[1,3]dioxol-4- or preferably -5-yl; and (xi) 2,3-dihydro-benzo[1,4]dioxin-5- or preferably -6-yl; whereby as $R_1$ the moieties mentioned under (ii), (viii), (ix), (x) and (xi) are especially preferred, while those under (i) and (iii) to (vii) are especially preferred as $R_2$. Where in any heterocyclyl moieties "unsaturated" is mentioned, this is intended to mean that the maximum number of non-cumulated double bonds is present in the ring system.

Halo (=halogeno) is preferably fluoro, chloro or bromo, if not indicated otherwise.

The symbols m and n each preferably stand for 1.

Due to the asymmetrical carbon atom(s) present in the compounds of formula I and their salts, the compounds may exist in optically active form as isolated enantiomers or in the form of mixtures of optical isomers, e.g. in form of racemic mixtures. All single optical isomers as well as their mixtures including the racemic mixtures are part of the present invention. Preferably, the compounds of the formula I are in the form of pure optical isomers.

Salts of compounds of formula I are especially acid addition salts (as basic groups, such as the nitrogen atoms in the piperazine and piperidine rings are present, or, where several salt-forming groups are present, can also be mixed salts, also with bases, or internal salts. Salts are especially pharmaceutically acceptable salts of compounds of formula I. Acid addition salts are formed, for example, from compounds of formula I with inorganic acids, for example hydrohalic acids, such as hydrochloric acid, sulfuric acid or phosphoric acid, or with organic carboxylic, sulfonic, sulfo or phospho acids or N-substituted sulfamic acids, for example fumaric acid or acetic acid, methanesulfonic acid, N-cyclohexylsulfamic acid (forming cyclamates) or with other acidic organic compounds, such as ascorbic acid. Acid groups in a compound of the formula I, such as carboxy, are, for example, salts thereof with suitable bases, such as non-toxic metal salts derived from metals of groups Ia, Ib, IIa and IIb of the Periodic Table of the Elements, for example sodium or potassium salts, or alkaline earth metal salts, for example magnesium or calcium salts, also zinc salts or ammonium salts, as well as salts formed with ammonia or organic amines or with quaternary ammonium compounds. Compounds of formula I having both acidic and basic groups can also form internal salts. For manufacturing, isolation and/or purification purposes, it is also possible to use pharmaceutically inacceptable salts, for example a perchlorate or picolinate salt.

Where compounds or a compound (especially of formula I) is mentioned herein, this is (if not explicitely mentioned otherwise) always intended to mean the free compound and/or a salt thereof, where salt-forming groups are present, and is also intended to comprise solvates of such a compound or salt, e.g. hydrates.

Compounds of formula I and their pharmaceutically acceptable acid addition salts, hereinafter referred to as agents of the invention, exhibit valuable pharmacological properties when tested in vitro using SRIF receptor expressing cell cultures and in animals, and are therefore useful as pharmaceuticals or for the preparation of pharmaceuticals.

In particular the agents of the invention bind to somatostatin receptors. More particularly they are orally active, non-peptide somatostatin sst1 receptor (previously called SSTR-1 receptor) antagonists. Among the preferred indications are: bipolar disorders, social phobias and memory impairment in various neurological disorders such as Alzheimer's disease, age associated memory impairment and other dementias. In addition, the compounds aim to treat attention deficit and hyperactivity disorders (ADHD). Further, the compounds are indicated for the treatment of aggressive states in a variety of conditions, including schizophrenia. Still further, the compounds are indicated for the treatment of negative symptoms of schizophrenia.

In addition, the agents of the invention may be useful for the treatment of tumors, for the treatment of vascular disorders and/or for the treatment of immunological diseases.

The basis for the indications can be confirmed by the range of standard tests as indicated below:

The agents of the invention can be shown to have high affinity and selectivity for somatostatin sst1 receptors (see, for example, Hoyer D, Bell G I, Berelowitz M, Epelbaum J, Feniuk W, Humphrey P P A, O'Carroll A M, Patel Y C, Schonbrunn A, Taylor J E, Reisine T (1995); classification and nomenclature of somatostatin receptors. TiPS, 16: 86-88) in cerebral cortex of rat and with recombinant human and mouse versions (showing a pKd in the range from about 6 to 9, preferably in the range from 7.8 to 9.0) as described (see, for example, Siehler S., K. Seuwen & D. Hoyer. Characterisation of human recombinant somatostatin receptors: 1) radioligand binding studies (1999) Naunyn Schmiedeberg's Arch Pharmacol, 360: 488-499).

The agents of the invention further can be shown to antagonise SRIF-14-induced inhibition of forskolin-stimulated adenylate cyclase activity (pKb=7.5-8.5) (see, for example, Siehler S. & D. Hoyer. Characterisation of human recombinant somatostatin receptors: 3) modulation adenylate cyclase activity. (1999) Naunyn Schmiedeberg's Arch Pharmacol, 360: 510-521) and/or SRIF-28 induced stimulation of luciferase activity and to be devoid of intrinsic activity at sst1 receptors (see D. Hoyer, C. Nunn, J. Hannon, P. Schoeffter, D. Feuerbach, E. Schuepbach, D. Langenegger, R. Bouhelal, K. Hurth, P. Neumann, T. Troxler, P. Pfaeffli (2004) SRA880, a non peptide somatostatin sst1 receptor antagonist, Neuroscience letters, 361 (1-3):132-5).

They can be shown to have significantly lower affinity for a range of neurotransmitter receptors and ligand-gated channels as determined in various radioligand being tests (see, for example, Kalkman H O, N Subramanian, D Hoyer (2001) Comprehensive radioligand binding profile of iloperidone: a broad spectrum dopamine/serotonin/norepinephrine receptor antagonist for the management of psychotic disorders. Neuropsychopharmacology, 25: 9104-914).

The agents of the invention can be shown to lower aggressive behaviour in two mice models for aggression, the matched aggressive male pair and aggressive resident encounters (1-10 mg/kg s.c. and 3-30 mg/kg/p.o.) (see Dixon A. K, Huber C, Lowe D A (1994): Clozapine Promotes Approach-Oriented behaviour in male Mice. J. Clin. Psychiatry. 55: (9) Suppl. B. 4-7). They also can be shown to reverse the social withdrawal characteristic of "intruder" mice exposed to attacks from aggressive residents. Following treatment with the compounds (1-10 mg/kg, s.c. or 3-30 mg/kg/p.o.), intruder mice can be shown to increase approach behaviour towards the aggressive opponent and decreased avoidance behaviour (see Dixon A. K, Huber C, Lowe D A (1994): Clozapine Promotes Approach-Oriented behaviour in male Mice. J. Clin Psychiatry. 55: (9) Suppl. B. 4-7). The agents of the invention, preferably when administered in a dose range from 0.03 to 3 mg/kg p.o., can be shown to enhance social exploration of "intruder" rats confronted with a "resident" rat similar to benzodiazepines (see Vassout A, Veenstra S, Hauser K, Ofner S, Brugger F, Schilling W, Gentsch C. (2000) NKP608: a selective NK-1 receptor antagonist with anxiolytic-like effects in the social interaction and social exploration test in rats. Regulatory Peptides 96, 7-16.). The marked anti-aggressive and sociotropic effects of the agents of the invention are mimicked by the anti-manic agents lithium and carbamazepine or valproate (see Dixon A K (1990) Ethopharmacology: A biological approach to the study of drug-induced changes in behaviour: Adv. study. Behaviour 19: 171-204. Dixon A K, Fisch H U, Huber C, Walser A (1989) Ethological studies in animals and man, their use in psychiatry. Pharmacopsychiatry 22 (suppl): 44-50).

The agents of the invention, preferably in a dosing range from 0.01 to 10 mg/kg, can be shown to improve the performance in step-down passive avoidance in mice (following both pre- and post-trial administration). They can be shown to enhance retrieval-performance in step-through passive avoidance (0.1-10 mg/kg p.o.) and partially counteracted E-shock-induced amnesia (0.01-10 mg/kg p.o.). The agents of the invention can be shown to specifically enhance social recognition of familiar, but not unfamiliar juvenile rats, preferably in a dosing range from 0.03 to −3 mg/kg p.o. Similarly, they can be shown to increase social recognition in mice, e.g. in the dosing range from 0.03 to −3 mg/kg p.o. (see Mondadori C., Jaekel J. and Preiswerk G., (1993) CGP 36742: the first orally active GABA B blocker improves the cognitive performance of mice, rats and rhesus monkeys. Behavioral and Neural Biology 60, 62-68. Thor D. H. and Holloway W. R., (1982) Social memory in the male laboratory rat. Journal of Comparative and Physiological Psychology, 96, 1000-1006). Thus, the agents of the invention can be shown to clearly increase learning, memory and attention.

In the rat primary observation test, the agents of the invention when tested at a dose of, for example, 30 mg/kg p.o. can be shown to exhibit CNS activating effects. Consistently, in the sleep-wakefulness cycle in rats, the agents of the invention (e.g. at 30 mg/kg p.o.) can be shown to induce a marked increase of the wakefulness phase during the initial three hours while decreasing the REM and classical sleep phases.

The positive effects on memory acquisition/retention, combined with the sociotropic and anti-aggressive components displayed by the agents of the invention, suggest that these will prove useful in the treatment of ADHD (attention deficit and hyperactivity disorders).

Agents of the invention are also effective in the treatment of various kinds of tumors, particularly of sst1 receptor bearing tumors, as indicated in proliferation tests with various different cancer cell lines and in tumor growth experiments in nude mice with hormone dependent tumors [see for example: G. Weckbecker et al., Cancer Research 1994, 54: 6334-6337]. Thus the compounds are indicated in the treatment of, for example, cancers of the breast, the prostate, the colon, the pancreas, the brain and the lung (small cell lung cancer).

For all the above mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 10 mg/kg animal body weight. In larger mammals, for example humans, an indicated daily dosage is in the range from about 5 to about 200 mg, preferably about 10 to about 100 mg of the compound conveniently administered in divided doses up to 4 times a day.

The agents of the invention may be administered in free form or in pharmaceutically acceptable salt form. Such salts may be prepared in conventional manner and exhibit the same order of activity as the free compounds.

Accordingly in a further aspect the present invention provides the agents of the invention for use in the diagostic and therapeutic (including prophylactic) treatment of the animal or human body, especially as pharmaceuticals, more specifically for treatment in the above-mentioned conditions, e.g. bipolar disorders, social phobias, memory impairment, attention deficit and hyperactive disorders, aggressive states and/or negative symptoms of schizophrenia.

The present invention furthermore provides a pharmaceutical composition comprising an agent of the invention in association with at least one pharmaceutically acceptable diluent or carrier. Such compositions may be formulated in conventional manner. Unit dosage forms contain, for example, from about 0.25 to about 50 mg of an agent according to the invention.

Agents of the invention may be administered by any conventional route, for example parenterally e.g. in form of injectable solutions or suspensions, or enterally, preferably orally, e.g. in the form of tablets or capsules.

The agents of the invention may alternatively be administered e.g. topically in the form of a cream, gel or the like, or by inhalation, e.g. in dry powder form.

Examples for compositions comprising an agent of the invention include, e.g. a solid dispersion, an aqueous solution, e.g. containing a solubilising agent, a microemulsion and a suspension of an agent of the invention. The composition may be buffered to a pH in the range of e.g. from 3.5 to 9.5, by a suitable buffer.

The agents of the invention can be administered either alone or in combination with other pharmaceutical agents effective in the treatment of conditions mentioned above.

Thus, the agents of the invention can be used for the treatment of depressive symptoms in combination with: tricyclics, MAO inhibitors, SSRI's, SNRI's, NK receptor antagonists, CRF-receptor antagonists, 5HT7 receptor-antagonists, mGlu receptor agonists/antagonist/modulators, GABA-A or GABA-A/B receptor agonist/antagonists or modulators, vasopressin receptor antagonists, electroconvulsive shock, sleep deprivation, or herbal medicine such as St. John's Wort.

The agents of the invention can also be used for the treatment of anxiety-symptoms in combination with: benzodiazepines including mitochondrial benzodiazepine-ligands, 5-HT1 A receptor agonists, SSRI's, SNRI's, NK receptor-antagonists, CRF receptor-antagonists, vasopressin receptor-antagonists, mGlu receptor agonists/antagonist/modulators, GABA-A or GABA-A/B receptor agonists/antagonists or modulators.

The agents of the invention can further be used for the treatment of any forms of dementia, including Alzheimer's disease (SDAT) in combination with: acetylcholine-esterase inhibitors, such as rivastigmine and donepezil, mixed acetylcholine/butyrylcholine esterase-inhibitors and nicotinic-alpha7-receptor agonists.

Moreover the agents of the invention can be used for the treatment of psychotic symptoms, including positive and negative symptoms in schizophrenia and schizoid type syndromes in combination with: any typical or atypical antipsychotic, such as clozapine or haloperidol, and nicotinic-alpha7-receptor agonists.

Furthermore the agents of the invention can be used for the treatment of bipolar disorders in combination with: any antimanic agent (e.g. Lithium, Carbamazepine, Valproate) or any atypical or typical antipsychotic.

The pharmaceutical compositions for separate administration of the combination partners and for the administration in a fixed combination, i.e. a single galenical composition comprising at least two combination partners according to the invention, can be prepared in a manner known per se and are thus suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

In particular, a therapeutically effective amount of each of the combination partners may be administered simultaneously or sequentially and in any order, and the components may be administered separately or as fixed combination.

Accordingly the invention also provides a combination comprising a therapeutically effective amount of an agent of the invention and a second drug substance, or a pharmaceutically acceptable salt thereof where salt-forming groups are present, said second drug substance being for example for use in any of the particular indications hereinbefore set forth.

The preferred indications are depression, anxiety and affective disorders, especially bipolar disorders, e.g. mania, social phobias, memory impairment, attention deficit, hyperactive disorders, aggressive states and/or negative symptoms of schizophrenia.

In accordance with the foregoing, the present invention also provides the use of an agent of the invention as a pharmaceutical, e.g. the use for the treatment of any one or more of the disorders mentioned above, especially of e.g. bipolar disorders, social phobias, memory impairment, attention deficit, hyperactive disorders, aggressive states and/or negative symptoms of schizophrenia.

Moreover the present invention provides the use of an agent of the invention for the manufacture of a medicament for the treatment of any one or more of the conditions or disorders mentioned above, e.g. bipolar disorders, social phobias, memory impairment, attention deficit, hyperactive disorders, aggressive states and/or negative symptoms of schizophrenia.

In still a further aspect the present invention provides a method for the treatment (this term wherever used above or below also comprising prophylaxis) of any one or more of the conditions or disorders mentioned above, e.g. bipolar disorders, social phobias, memory impairment, attention deficit, hyperactive disorders, aggressive states and/or negative symptoms of schizophrenia, in a subject in need of such treatment, which comprises administering to such subject a therapeutically effective amount of an agent of the invention.

In yet a further aspect, the present invention relates to a method of preparing a pharmaceutical preparation for the treatment of any one or more of the conditions or disorders mentioned above, comprising admixing an agent of the invention with one or more carriers and/or diluents.

Preferred compounds of the invention have high affinity for somatostatin receptors, independently of the species, the expression system and the radioligand used, and are $sst_1$ selective.

They can be shown to significantly increase the duration of social contacts of the intruder rat towards the resident rat. In the social recognition test in mice, the compounds can be shown to exhibit a specific enhancing effect on the learning/memory performance.

PREFERRED EMBODIMENTS OF THE INVENTION

Preferred is a compound of the formula I wherein $R_1$ is a moiety selected from the group consisting of

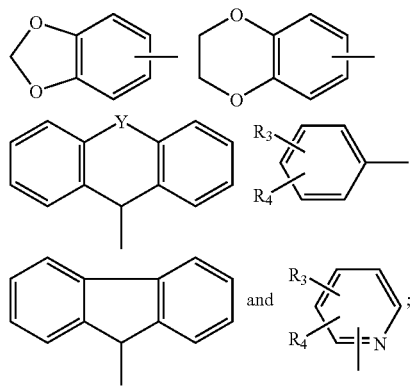

R2 is a moiety selected from the group consisting of moieties of the formulae

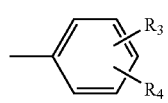 (a)

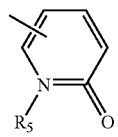 (b)

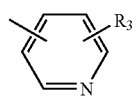 (c)

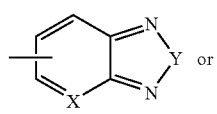 (d) or

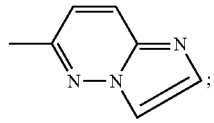 (e)

wherein
X is CH or N,
Y is O or S,
$R_3$ and $R_4$, independently of each other, are hydrogen, hydroxy, halogen, nitro, cyano, trifluoromethyl, $C_1$-$C_4$-alkyl or $C_1$-$C_4$-alkoxy, and
$R_5$ is hydrogen or $C_1$-$C_4$-alkyl, and each of n and m is, independently of the other, 1 or 2, preferably 1; or an (especially pharmaceutically acceptable) salt thereof, as well as any one or more of the combinations, uses and methods mentioned above with such compound or salt.

Most preferred is a compound of the formula selected from the compounds mentioned in the examples, or an (especially pharmaceutically acceptable) salt thereof, as well as any one or more of the combinations, uses and methods mentioned above with such compound or salt.

Manufacturing Processes

The compounds of the invention can be prepared in analogy to methods that, per se, though not for the compounds of formula I, are known in the art.

In the following description of preferred manufacturing processes for compounds of the formula I, R1, R2, m and n are as defined for compounds of the formula I or preferred versions thereof, as given above and below.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the H$^+$ form, depending on the type of reaction and/or reactants at reduced, normal, or elevated temperature, for example in the range from −100° C. to about 190° C., preferably from about −80° C. to about 150° C., for example at −80 to −60° C., at room temperature, at −20 to 40° C. or at the boiling point of the solvent used, under atmospheric pressure or in a closed vessel, where appropriate or expedient under pressure, and/or in an inert atmosphere, for example under argon or nitrogen.

The solvents from which those solvents that are suitable for any particular reaction may be selected include, for example, water, esters, such as lower alkyl-lower alkanoates, for example ethyl acetate, ethers, such as aliphatic ethers, for example diethyl ether, or cyclic ethers, for example tetrahydrofuran, liquid aromatic hydrocarbons, such as benzene or toluene, alcohols, such as methanol, ethanol or 1- or 2-propanol, or phenols, such as phenol, nitriles, such as aceto nitrile, halogenated hydrocarbons, such as methylene chloride, acid amides, such as dimethylformamide, bases, such as heterocyclic nitrogen bases, for example pyridine, carboxylic acid anhydrides, such as lower alkanoic acid anhydrides, for example acetic anhydride, cyclic, linear or branched hydrocarbons, such as cyclohexane, hexane or iso pentane, or mixtures of those solvents, for example aqueous solutions, unless otherwise indicated in the description of the processes. Such solvent mixtures may also be used in working up, for example by chromatography or partitioning.

In the following description of some preferred methods of preparation for compounds of the formula I or salts thereof and for starting materials as well as in other processes mentioned above and below, functional groups that are not to participate in the respective reaction and which would disturb the desired reaction or lead to side reactions are present in protected form, where required. The protection of functional groups and the respective protecting groups are, for example, described in the literature, for example in standard textbooks such as J. F. W. McOmie, "Protective Groups in Organic Chemistry", Plenum Press, London and New York 1973; in T. W. Greene and P. G. M. Wuts, "Protective Groups in Organic Synthesis", Third edition, Wiley, New York 1999; in "The Peptides"; Volume 3 (editors: E. Gross and J. Meienhofer), Academic Press, London und New York 1981, in "Methoden der organi-schen Chemie", Houben Weyl, 4. Ausgabe, Band 15/I, Georg Thieme Verlag, Stuttgart 1974, in H.-D. Jakubke and H. Jescheit, "Aminosäuren, Peptide, Proteine", Verlag Chemie, Weinheim, Deerfield Beach, and Basel 1982, and/or in Jochen Lehmann, "Chemie der Kohlenhydrate: Monosaccharide und Derivate", Georg Thieme Verlag, Stuttgart 1974. The removal of protecting groups is possible under customary conditions, preferably as described in the mentioned references, and at appropriate reaction stages and steps. The groups that have to be protected are known to the person having skill in the art, and therefore the introduction, presence and/or removal of protecting groups are mentioned only if very important for the process steps described below. Although not especially mentioned, it is clear that the starting materials can also be used in the form of salts where salt-forming groups are present and the formation of salts does not lead to undesired reactions.

Preferably, a compound of the formula I is prepared by a) reacting an N-acryloyl-piperazine compound of the formula II,

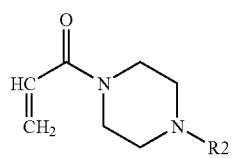

(II)

wherein R2 is as defined for a compound of the formula I, with an amino compound of the formula III,

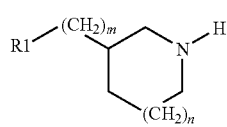

(III)

wherein R1, m and n are as defined for a compound of the formula I above or below, or b) reacting a carbonic acid compound of formula IV

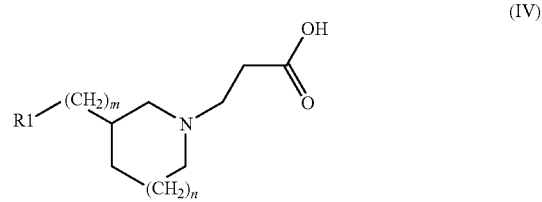

(IV)

wherein R1, m and n are as defined for a compound of the formula I above or below, or a reactive derivative thereof, with a piperazine compound of the formula V,

(V)

wherein R2 is as defined for a compound of the formula I above or below;

and, if desired, transforming a compound of formula I into a different compound of formula I, transforming a salt of an obtainable compound of formula I into the free compound or a different salt, transforming an obtainable free compound of formula I into a salt, and/or separating obtainable mixtures of isomers of compounds of formula I into the individual isomers.

Reaction a) preferably takes place in the presence of an appropriate solvent that itself is not reactive under the reaction conditions, such as an ether, especially a cyclic ether, e.g. tetrahydrofurane, preferably at a temperature in the range from 0 to 50° C., e.g. at room temperature, preferably in the presence of a base, especially a tertiary nitrogen base, such as a trilower alkylamine, e.g. triethylamine.

In reaction b), the carbonic acid of the formula IV is either converted in situ into a reactive derivative, e.g. by dissolving the compounds of formulae IV and V in a suitable solvent, for example N,N-dimethylformamide, N,N-dimethylacetamide, N-methyl-2-pyrrolidone, methylene chloride, or a mixture of two or more such solvents, and by the addition of a suitable base, for example triethylamine, diisopropylethylamine (DIEA) or N-methylmorpholine and a suitable coupling agent that forms a preferred reactive derivative of the carbonic acid of formula III in situ, for example dicyclohexylcarbodi-imide/1-hydroxybenzotriazole (DCC/HOBT); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); or 1-(3-dimethyl-aminopropyl)-3-ethylcarbodiimide hydrochloride (EDC). For review of other possible coupling agents, see e.g. Klauser; Bodansky, *Synthesis* 1972, 453-463. The reaction mixture is preferably stirred at a temperature of between approximately −20 and 50° C., especially between 0° C. and room temperature, to yield a compound of formula I. Alternatively, the carbonic acid of the formula IV is used in the form of a reactive derivative, e.g. as the carbonic acid halide, such as chloride, as an anhydride with a carbonic acid, e.g. with a $C_1$-$C_7$-alkanoic acid, as an active ester, or in the form of an alkali metal salt, e.g. a sodium, lithium or potassium salt. In both cases, the reaction can preferably be carried out under an inert gas, e.g. nitrogen or argon.

Working up the reaction mixtures according to the above processes and purification of the compounds thus obtained may be carried out in accordance to known procedures.

Optional Reactions/Conversions:

Compounds of the formula I may be converted into different compounds of the formula I. For example, lower alkoxycarbonyl substituents may be converted into carboxyl by saponification, nitro substituents may be hydrogenated to amino.

Salts of a compound of formula I with a salt-forming group may be prepared in a manner known per se from the free compound. For example, acid addition salts of compounds of formula I may be obtained by treatment of the free compound with an acid or with a suitable anion exchange reagent. Salts of a compound of the formula I can usually be converted to free compounds, e.g. by treating with suitable basic agents, for example with alkali metal carbonates, hydrogencarbonates, or hydroxides, typically potassium carbonate or sodium hydroxide. Salts of a compound of the formula I may also be converted into different salts by treatment with appropriate salts. e.g. using a molar excess thereof over the salt of a compound of the formula I.

Stereoisomeric mixtures of a compound of the formula I, e.g. mixtures of enantiomers, as well as of starting materials can be separated into their corresponding isomers in a manner known per se by means of suitable separation methods. Enantiomeric mixtures for example may be separated into their individual enantiomers through the formation of diastereomeric salts, for example by salt formation with an enantiomer-pure chiral acid, or by means of chromatography, for example by HPLC, using chromatographic solid phases with chiral ligands.

Starting Materials:

In view of the close relationship between the starting materials (starting materials and intermediates) in free form and in the form of their salts, any reference hereinbefore and hereinafter to a free compound or a salt thereof is to be understood as meaning also the corresponding salt or free compound or salt/free compound mixture, respectively, where appropriate and expedient.

The starting materials are known in the art or can be prepared according to or in analogy to methods that are known in the art or in the examples.

A starting material of the formula II, or a salt thereof, can be prepared by reacting a piperidine compound of the formula VI,

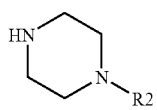

(VI)

wherein R2 is as defined for a compound of the formula I, with acrylic acid or an active derivative thereof, preferably acrylic acid halide, e.g. the chloride, in an appropriate solvent, e.g. a halogenated hydrocarbon, such as methylene chloride, preferably at lowered temperatures, such as in the range from −20 to 15° C., e.g. at about = to 5° C., preferably in the presence of a base, such as a tertiary nitrogen base, e.g. a tri-$C_1$-$C_7$-alkylamine, for example triethylamine.

The starting materials of the formula VI can be produced by or in analogy to methods that are known in the art, for example in analogy to the method described in Example 1 by reaction of compounds of the formula VII, R2-Hal  (VII)

wherein R2 is as defined for a compound of the formula I, especially substituted aryl, and Hal is halo, especially fluoro, with piperazine, e.g. in an appropriate aprotic solvent, such as a nitrile, for example acetonitrile, in the presence of a base, e.g. an alkali metal carbonate, such as potassium carbonate, at preferred temperatures in the range from 0 to 50° C., e.g. at about room temperature.

A compound of the formula III, or a salt thereof, can be prepared by reducing a lactame compound of the formula VIII,

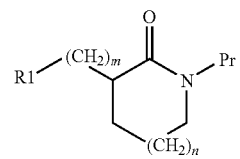

(VIII)

wherein R1, m and n are as defined for a compound of the formula I and Pr is an amino protecting group, e.g. benzyl, with an appropriate complex hydride, e.g. lithium aluminium hydride, in an appropriate solvent, such as an ether, e.g. tetrahydrofurane, at preferred temperatures from 10° C. to the reflux temperature, e.g. from room temperature to the reflux temperature of the mixture; and subsequently removing the protecting group, e.g. benzyl, preferably by hydrogenation in the presence of a noble metal catalyst, e.g. palladium on charcoal (Pd/C), in an appropriate solvent, e.g. a mixture of an alcohol, such as methanol, and a carboxylic acid, e.g. acetic acid, at preferred temperatures in the range from 0 to 50° C., e.g. at about room temperature.

A compound of the formula VIII can, for example, be obtained by reacting a compound of the formula IX,

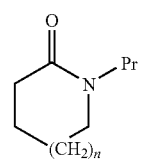

(IX)

wherein Pr and n are as just defined, in an appropriate solvent, such as an ether, e.g. tetrahydrofurane, in the absence or presence of one or more further solvents, e.g. lower alkanes or lower cacloalkanes, such as hexane or cyclohexane, at low temperatures, e.g. in the range from −80 to −50° C., such as about −70° C., preferably under an inert gas, such as argon, first in the presence of a metalating agent, e.g. litium butanide, such as sec.-butyllithium, and then with a compound of the formula

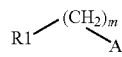

wherein R1 and m are defined as for a compound of the formula I (where m is preferably 1 or 2) and A is halo, especially bromo.

A starting material of the formula IV can, for example, be obtained by reacting a compound of the formula III, which can be obtained as described above, with a carboxyl protected form of acrylic acid in analogy to the reaction conditions mentioned above under process a) or of a 3-halo-propionic acid, such as of a 3-bromo-propionic acid, and subsequent removal of the protecting group.

Starting materials of the formula V are identical to those of the formula VI described above.

Other starting materials can be obtained according to or in analogy to known procedures or are commercially available.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention there are preferably used those starting materials which result in the compounds of formula I described at the beginning as being especially valuable. Special preference is given to reaction conditions and processes of manufacture that are analogous to those mentioned in the Examples. The invention also relates to novel starting materials described above and below that are useful in the synthesis of compounds of the formula I.

EXAMPLES

The following Examples serve to illustrate the invention without limiting the scope thereof:

| Abbreviations: | |
|---|---|
| abs. | absolute |
| AcOH | acetic acid |
| AcOEt | ethyl acetate |
| aq. | Aqueous |
| sec.-BuLi | sec.-butyllithium (lithium-2-butanide) |
| Celite® | filtering aid based on kieselguhr (Celite Corporation, Lompoc, USA) |
| d | day(s) |
| DMSO | dimethyl sulfoxide |
| ESI-MS | Electrospray Ionisation Mass Spectrometry |
| ether | diethylether |
| EtOH | ethanol |
| h | hour(s) |
| HPLC | high performance liquid chromatography |
| MeOH | methanol |
| min | minute(s) |
| MPLC | medium pressure liquid chromatography |
| $^1$H-NMR | Proton Nuclear Magnetic Resonance |
| Pd/C | Palladium on charcoal |
| rt | room temperature |
| sat. | saturated |
| THF | tetrahydrofurane |

Solvent relations, e.g. in eluents or solvent mixtures, are given in v/v (volume by volume), temperatures in ° C. (uncorrected).

Example 1

(+)-4-{4-[3-(3-Benzo[1,3]dioxol-5-ylmethyl-piperidin-1-yl)-propionyl]-piperazin-1-yl}-2-fluoro-benzonitrile A solution of 4-(4-acryloyl-piperazin-1-yl)-2-fluoro-benzonitrile (0.125 g, 0.48 mmol), (+)-3-benzo[1,3]dioxol-5-ylmethyl-piperidine (0.106 g, 0.48 mmol) and triethylamine (0.088 ml, 0.629 ml) in THF (1.6 ml) is stirred at rt for 25 h. The mixture is diluted with CH$_2$Cl$_2$ and washed with sat. aq. Na$_2$CO$_3$ solution The organic layer is separated off, dried over Na$_2$SO$_4$ and evaporated. The residue is purified by MPLC (60 g silica gel, eluent CH$_2$Cl$_2$:MeOH 9:1) to give the title compound, (+)-4-{4-[3-(3-benzo[1,3]dioxol-5-ylmethyl-piperidin-1-yl)-propionyl]-piperazin-1-yl}-2-fluoro-benzonitrile, as a colourless foam:

$^1$H-NMR (400 MHz, DMSO): δ=7.68-7.61 (m, 1H), 6.99-6.93 (m, 1H), 6.89-6.84 (m, 1H), 6.83-6.79 (m, 1H), 6.77-6.74 (m, 1H), 6.64-6.59 (m, 1H), 5.97 (s, 2H), 3.62-3.54 (m, 4H), 3.50-3.37 (m, 4H), 2.77-2.64 (m, 2H), 2.51-2.33 (m, 6H), 1.96-1.87 (m, 1H), 1.74-1.52 (m, 4H), 1.43-1.34 (m, 1H), 0.94-0.84 (m, 1H); $[\alpha]_D^{rt}$=+14.7° (c=0.5, EtOH), ESI-MS M+H$^+$=479.3; optical purity >99.9%, as determined by HPLC comparison with the racemate using a Chiralcel® OD-RH 150×4.6 mm column (Daicel Chiral Technologies, Inc., Exton USA; a chiral stationary phase), eluent CH$_3$CN+ 0.1% diethylamine, flow rate 0.8 ml/min, UV detection (226 nM), retention time 4.8 min.

The starting materials are prepared as follows:

a) (−)-3-Benzo[1,3]dioxol-5-ylmethyl-1-benzyl-piperidin-2-one

1-Benzyl-piperidin-2-one (4.8 g, 25.4 mmol) in abs. THF (200 ml) is cooled to −70° C.; sec.-BuLi (23.4 ml of a 1.3 M solution in cyclohexane; 30.4 mmol) is added dropwise under an Ar atmosphere and the mixture is stirred at −70° C. for 30 min. A solution of 5-bromomethyl-benzo[1,3]dioxole (see Harrowven et al., Tetrahedron (2001), 57(29), 4447) (8.0 g, 37.2 mmol) in abs. THF (80 ml) is added dropwise, stirring is continued at −70° C. for 3 h, then at rt for 15 h. sat. aq. NH$_4$Cl solution is added, the organic layer is separated, dried over Na$_2$SO$_4$ and evaporated. The oily residue is purified by MPLC (140 g silica gel, eluent cyclohexane, then cyclohexane:AcOEt 7:3) to give 3-benzo[1,3]dioxol-5-ylmethyl-1-benzyl-piperidin-2-one as a yellow oil. Preparative resolution using a Chiralpak AD 5×50 cm/20 µm column (Daicel Chiral Technologies, Inc., Exton USA; a chiral stationary phase); eluent hexane: isopropanol 90:10; flow 80 ml/min; UV detection (210 nM) gives (−)-3-benzo[1,3]dioxol-5-ylmethyl-1-benzyl-piperidin-2-one ($[\alpha]_D^{rt}$=−61.1° (c=0.5, EtOH)).

b) (+)-3-Benzo[1,3]-dioxol-5-ylmethyl-1-benzyl-piperidine

To a solution of (−)-3-benzo[1,3]dioxol-5-ylmethyl-1-benzyl-piperidin-2-one (1.73 g, 5.3 mmol) in THF (21 ml), LiAlH$_4$ (6.5 ml of a 1 M solution in THF, 6.5 mmol) is added dropwise at rt. The mixture is refluxed for 2.5 h, cooled to rt, quenched with water and filtered over Celite®. The filtrate is evaporated, the residue dissolved in AcOEt, washed with water and brine, and the aq. layers are reextracted with AcOEt, the combined organic layers are dried over Na$_2$SO$_4$ and evaporated to give (+)-3-benzo[1,3]dioxol-5-ylmethyl-1-benzyl-piperidine ($[\alpha]_D^{rt}$=28.2° (c=0.5, EtOH)).

c) (+)-3-Benzo[1,3]-dioxol-5-ylmethyl-piperidine 1.40 g (4.5 mmol) of (+)-3-benzo[1,3]dioxol-5-ylmethyl-1-benzyl-piperidine is dissolved in 35 ml MeOH and 1 ml AcOH and hydrogenated over Pd/C 10% (0.3 g) for 2 d until hydrogen absorption is complete. The mixture is filtered over Celite®, and the filtrate is evaporated, diluted with CH$_2$Cl$_2$, washed with sat. aq. Na$_2$CO$_3$ solution and evaporated to give (+)-3-benzo[1,3]dioxol-5-ylmethyl-piperidine ([α]$_D^{rt}$=5.90 (c=0.5, DMSO)) which is used without further purification.

d) 2-Fluoro-4-(piperazin-1-yl)-benzonitrile

Piperazine (20.0 g, 232.3 mmol) and K$_2$CO$_3$ (16.0 g, 118.5 mmol) are dissolved in CH$_3$CN (85 ml). 2,4-Difluoro-benzonitrile (8.5 g, 61.1 mmol) is added and the mixture is stirred for 2 h at rt, then diluted with AcOEt and washed with water. The organic layer is separated, dried over Na$_2$SO$_4$ and evaporated. Excess piperazine is removed by MPLC (100 g silica gel, eluent CH$_2$Cl$_2$:MeOH 85:15). A second chromatographic purification (300 g silica gel, eluent toluene:EtOH:AcOH 4:4:1) yields the acetate salt of 2-fluoro-4-(piperazin-1-yl)-benzonitrile that is crystallized from AcOEt, filtered off and washed with ether. The free base is isolated by extraction with sat. aq. Na$_2$CO$_3$ solution/AcOEt.

e) 4-(4-Acryloyl-piperazin-1-yl)-2-fluoro-benzonitrile

A solution of 2-fluoro-4-(piperazin-1-yl)-benzonitrile (0.53 g, 2.56 mmol) and triethylamine (0.5 ml, 3.59 mmol) in CH$_2$Cl$_2$ (13 ml) is added dropwise to a cooled solution (0-5° C.) of acryloyl chloride (0.25 ml, 3.15 mmol) in CH$_2$Cl$_2$ (3 ml). After complete addition, the mixture is stirred at rt for 1 h, sat. aq. Na$_2$CO$_3$ solution is added and stirring is continued for 20 min. The organic layer is separated off, dried over Na$_2$SO$_4$ and evaporated. Upon addition of AcOEt, 4-(4-acryloyl-piperazin-1-yl)-2-fluoro-benzonitrile crystallizes out, is filtered off, washed with AcOEt and air-dried.

In analogy to example 1 and/or the methods mentioned above, the following examples are prepared:

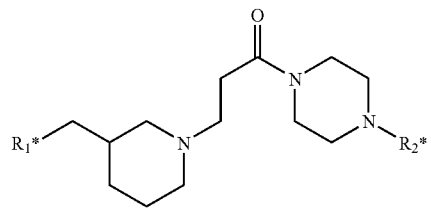

| Example No. | R$_1$* | R$_2$* | α$_0$ (c = 0.5) | salt form | mp. (° C.) |
|---|---|---|---|---|---|
| 2 | benzo[1,3]dioxol-5-yl | benzo[1,2,5]oxadiazol-5-yl* | positive (EtOH) | free base | n.d. (amorphous) |
| 3 | benzo[1,3]dioxol-5-yl | 4-cyano-phenyl | (rac.) | phosphate | 115-117 |
| 4 | benzo[1,3]dioxol-5-yl | 4-[1,2,5]-thiadiazolo-[3,4-b]pyridin-5-yl** | positive (DMSO) | free base | 96-101 |
| 5 | benzo[1,3]dioxol-5-yl | 3,4-difluoro-phenyl | (rac.) | free base | 188-192 |
| 6 | benzo[1,3]dioxol-5-yl | 4-cyano-2,6-difluoro-phenyl | (rac.) | phosphate | 115-125 |
| 7 | benzo[1,3]dioxol-5-yl | 4-nitro-phenyl | (rac.) | free base | n.d. (amorphous) |
| 8 | benzo[1,3]dioxol-5-yl | 2-pyridyl | (rac.) | phosphate | 101-108 |
| 9 | benzo[1,3]dioxol-5-yl | 1-methyl-6-oxo-1,6-dihydro-pyridin-2-yl | (rac.) | phosphate | 118-125 |
| 10 | benzo[1,3]dioxol-5-yl | imidazo[1,2-b]pyridazin-6-yl*** | (rac.) | free base | 107-118 |
| 11 | 6-methoxy-pyridin-3-yl | benzo[1,2,5]oxadiazol-5-yl | (rac.) | hydrochloride | n.d. (amorphous) |
| 12 | 4-fluoro-phenyl | benzo[1,2,5]oxadiazol-5-yl | (rac.) | hydrochloride | n.d. (amorphous) |
| 13 | 2,3-dihydro-benzo[1,4]dioxin-6-yl | benzo[1,2,5]oxadiazol-5-yl | positive (MeOH) | hydrochloride | 96 (decomposition) |
| 14 | 2-methoxy-pyridin-3-yl | benzo[1,2,5]oxadiazol-5-yl | (rac.) | phosphate | 143-150 |
| 15 | 2,6-dimethoxy-pyridin-3-yl | benzo[1,2,5]oxadiazol-5-yl | Positive (MeOH) | free base | n.d. (amorphous) |
| 16 | 9H-thioxanthene-9-yl | 4-nitro-phenyl | (rac.) | fumarate | 215-219 |
| 17 | pyridin-3-yl | benzo[1,2,5]oxadiazol-5-yl | (rac.) | hydrochloride | n.d. (oil) |

(rac): These compounds are present as racemates.
n.d. = not determined.
*This moiety has the formula

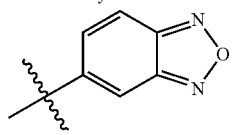

-continued

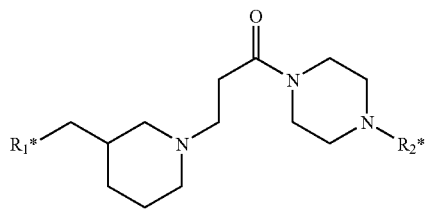

| Example No. | R₁* | R₂* | $\alpha_0$ (c = 0.5) | salt form | mp. (° C.) |
|---|---|---|---|---|---|

**This moiety has the formula

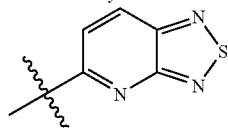

***This moiety has the formula

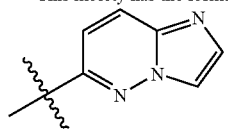

Example 17

Soft Capsules 5000 soft gelatin capsules, each comprising as active ingredient 0.05 g of one of the compounds of formula I mentioned in any one of the preceding Examples, are prepared as follows:

| Composition | |
|---|---|
| Active ingredient | 250 g |
| Lauroglycol | 2 liters |

Preparation process: The pulverized active ingredient is suspended in Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

Example 18

Tablets Comprising Compounds of the Formula I

Tablets, comprising, as active ingredient, 100 mg of any one of the compounds of formula I of Examples 1 to 16 are prepared with the following composition, following standard procedures:

| Composition | |
|---|---|
| Active Ingredient | 100 mg |
| crystalline lactose | 240 mg |
| Avicel | 80 mg |

-continued

| Composition | |
|---|---|
| PVPPXL | 20 mg |
| Aerosil | 2 mg |
| magnesium stearate | 5 mg |
| | 447 mg |

Manufacture: The active ingredient is mixed with the carrier materials and compressed by means of a tabletting machine (Korsch EKO, Stempeldurchmesser 10 mm).

Avicel® is microcrystalline cellulose (FMC, Philadelphia, USA).

PVPPXL is polyvinylpolypyrrolidone, cross-linked (BASF, Germany).

Aerosil® is silcium dioxide (Degussa, Germany).

What is claimed is:

1. A compound of the formula I

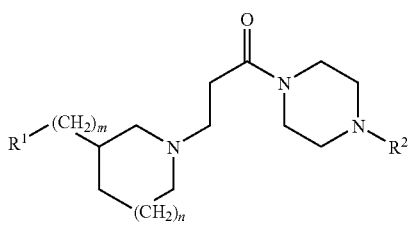

(I)

wherein

R¹ and R² are independently selected from the group consisting of phenyl that is unsubstituted or substituted by one or more substituents independently selected from cyano, $C_1$-$C_7$-alkoxy, nitro and halo, fluorenyl pyridinyl that is unsubstituted or substituted by one or more substituents independently selected from hydroxy, halo, nitro, cyano, trifluoromethyl, $C_1$-$C_4$-alkyl and $C_1$-$C_4$-alkoxy, 1-alkyl-oxo-dihydropyridinyl, benzo[1,2,5]oxadiazolyl, benzo[1,2,5]thiadiazolyl, imidazo[1,2-b]pyridazin-8-, -7- or -6-yl, 4-[1,2,5]-thiadiazolo-[3,4-b]pyridin-7-, -6- or -5-yl, xanthenyl, thioxanthenyl, benzo[1,3]dioxol-4- or -5-yl, and 2,3-dihydro-benzo[1,4]dioxin-5- or -6-yl;

and each of n and m is 1;

or a salt thereof.

2. A compound of the formula I according to claim 1, wherein $R^1$ is a moiety selected from the group consisting of

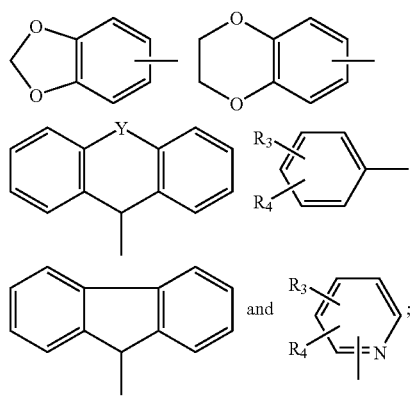

$R^1$ is a moiety selected from the group consisting of moieties of the formulae

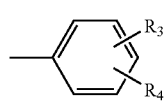
(a)

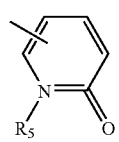
(b)

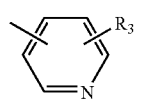
(c)

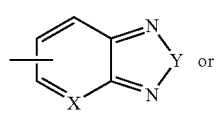
(d)

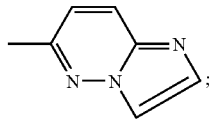
(e)

X is CH or N,

Y is O or S, $R_3$ and $R_4$, independently of each other, are hydrogen, hydroxy, halogen, nitro, trifluoromethyl, $C_1$-$C_4$-alkyl or $C_1$-$C_4$-alkoxy, and $R_5$ is hydrogen or $C_1$-$C_4$-alkyl.

3. A compound of the formula I, selected from the group consisting of the compound named (+)-4-{4-[3-(3-benzo[1,3]dioxol-5-ylmethyl-piperidin-1-yl)-propionyl]-piperazin-1-yl}-2-fluoro-benzonitrile and the compounds 2 to 16 in the following table of the formula:

| Compound No.. | $R_1$* | $R_2$* | Enantiomer or racemate |
|---|---|---|---|
| 2 | benzo[1,3]dioxol-5-yl | benzo[1,2,5]oxadiazol-5-yl | (+)-enantiomer |
| 3 | benzo[1,3]dioxol-5-yl | 4-cyano-phenyl | racemate |
| 4 | benzo[1,3]dioxol-5-yl | 4-[1,2,5]-thiadiazolo-[3,4-b]pyridin-5-yl** | (+)-enantiomer |
| 5 | benzo[1,3]dioxol-5-yl | 3,4-difluoro-phenyl | racemate |
| 6 | benzo[1,3]dioxol-5-yl | 4-cyano-2,6-difluoro-phenyl | racemate |
| 7 | benzo[1,3]dioxol-5-yl | 4-nitro-phenyl | racemate |
| 8 | benzo[1,3]dioxol-5-yl | 2-pyridyl | racemate |
| 9 | benzo[1,3]dioxol-5-yl | 1-methyl-6-oxo-1,6-dihydro-pyridin-2-yl | racemate |
| 10 | benzo[1,3]dioxol-5-yl | imidazo[1,2-b]pyridazin-6-yl*** | racemate |
| 11 | 6-methoxy-pyridin-3-yl | benzo[1,2,5]oxadiazol-5-yl | racemate |
| 12 | 4-fluoro-phenyl | benzo[1,2,5]oxadiazol-5-yl | racemate |
| 13 | 2,3-dihydro-benzo[1,4]dioxin-6-yl | benzo[1,2,5]oxadiazol-5-yl | (+)-enantiomer |
| 14 | 2-methoxy-pyridin-3-yl | benzo[1,2,5]oxadiazol-5-yl | racemate |
| 15 | 2,6-dimethoxy-pyridin-3-yl | benzo[1,2,5]oxadiazol-5-yl | (+)-enantiomer |
| 16 | 9H-thioxanthene-9-yl | 4-nitro-phenyl | racemate | or a salt thereof.

4. A compound of formula (I) according to claim 1 in the form of a pure Enantiomer.

5. A pharmaceutical composition comprising a compound of the formula (I), or a pharmaceutically acceptable salt thereof, according to claim 1 and a pharmaceutically acceptable carrier.

* * * * *